United States Patent
Nicol et al.

[11] Patent Number: 5,413,609
[45] Date of Patent: May 9, 1995

[54] METACARPAL-PHALANGEAL (MCP) JOINT PROSTHESIS

[75] Inventors: Alexander C. Nicol, Glasgow; Donald C. Marsden, Faringdon; William A. Souter, Edinburgh, all of United Kingdom

[73] Assignee: University of Strathclyde, Glasgow, Scotland

[21] Appl. No.: 960,382
[22] PCT Filed: Jul. 3, 1991
[86] PCT No.: PCT/GB91/01078
§ 371 Date: Mar. 15, 1993
§ 102(e) Date: Mar. 15, 1993
[87] PCT Pub. No.: WO92/00709
PCT Pub. Date: Jan. 23, 1992

[30] Foreign Application Priority Data
Jul. 7, 1990 [GB] United Kingdom ............... 9015030

[51] Int. Cl.6 ................................................ A61F 2/42
[52] U.S. Cl. ............................................ 623/21; 623/18
[58] Field of Search ............................ 623/21, 18, 20

[56] References Cited

U.S. PATENT DOCUMENTS

| | | |
|---|---|---|
| 4,340,978 | 7/1982 | Buechel et al. |
| 4,725,280 | 2/1988 | Laure .................................. 623/21 |
| 4,784,661 | 11/1988 | Beckenbaugh et al. ............ 623/21 |
| 5,037,440 | 8/1991 | Koenig ............................... 623/21 |

FOREIGN PATENT DOCUMENTS

| | | | |
|---|---|---|---|
| 0310483 | 4/1989 | European Pat. Off. | |
| 2605878 | 5/1988 | France. | |
| 2126097 | 3/1984 | United Kingdom ............... 623/21 |
| 2160779A | 1/1986 | United Kingdom. | |
| 89/09580 | 10/1989 | United Kingdom. | |

Primary Examiner—David H. Willse
Attorney, Agent, or Firm—Bell Seltzer Park

[57] ABSTRACT

A joint prosthesis for a human or animal body, which comprises first (20) and second (40) components each made of bio-compatible material and adapted for secural to respective bones (13,14) of the body in the vicinity of a natural joint (16) after surgical excision of the natural joint (16). The components (20,40) of the prothesis (12) are unattached to each other and, in use, are held together to form the joint by the natural ligaments, tendons and muscles of the body in the vicinity of the natural joint (16). The first component (20) comprises a stem (21) for reception by a bone cavity and a bulbous head (22) presenting a three-dimensionally curved convex articulation surface (23) which in the sagittal plane has a radius of curvature which changes within the arc length of the surface in that plane and which has a length of at least 90°. The second component (40) comprises a stem (41) for reception by a bone cavity and a head (42) presenting a three-dimensionally curved concave articulation surface (43) which is dimensioned to slide over the convex surface (23) substantially along the 90° arc length. This provides flexing movement of the prosthetic joint with the instantaneous center of rotation of the joint changing during the flexing movement due to the changes of radius of curvature so as to change the distance between the respective bones (13,14) and thereby allow natural collateral ligament function around the prosthetic joint to aid flexor muscle effect when the joint is extended and extensor muscle effect when the joint is flexed.

5 Claims, 4 Drawing Sheets

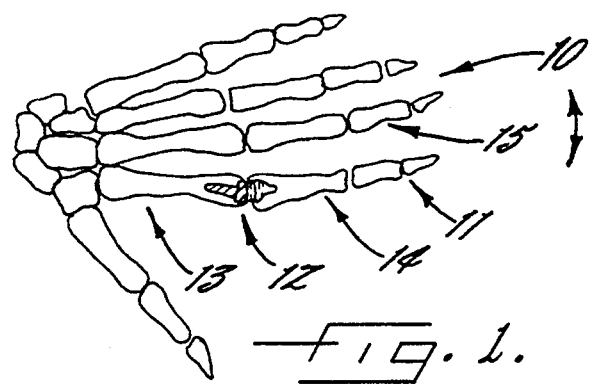
Fig. 1.
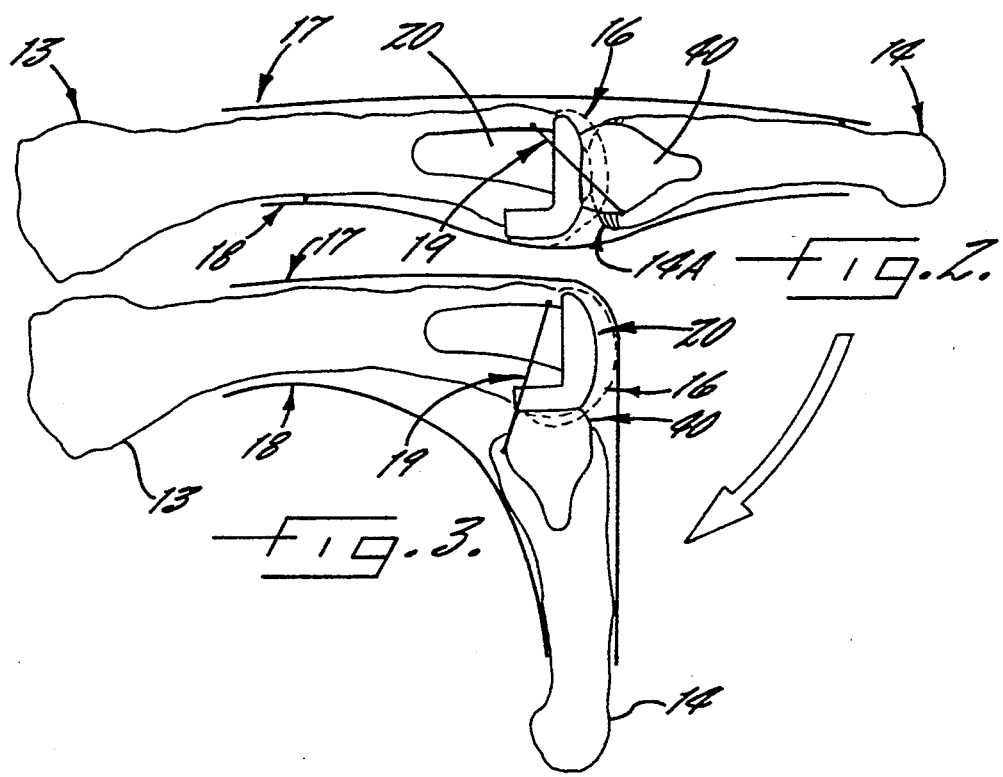
Fig. 2.
Fig. 3.
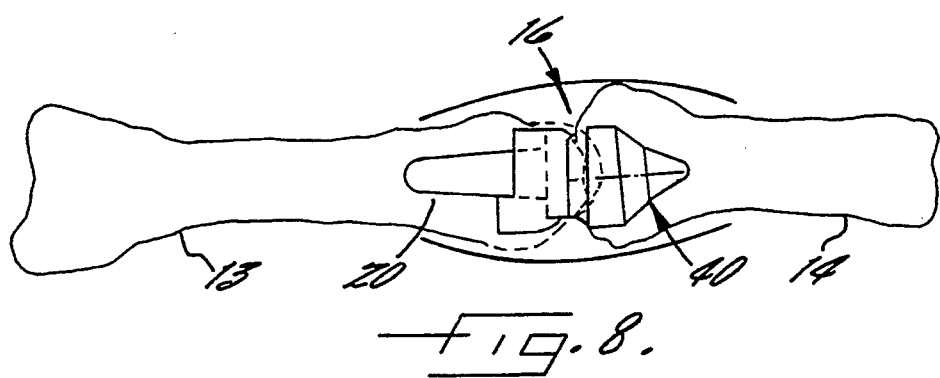
Fig. 8.

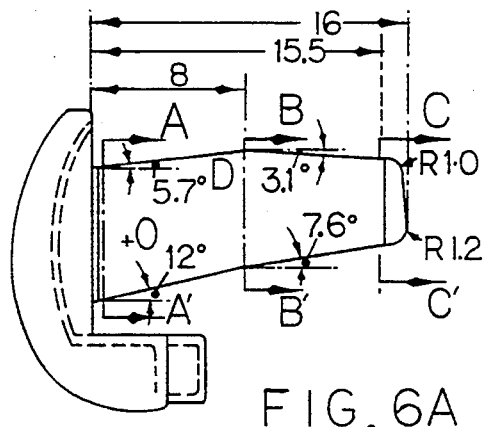
FIG. 6A
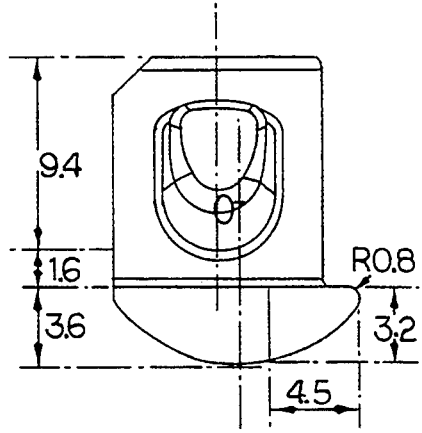
FIG. 6C
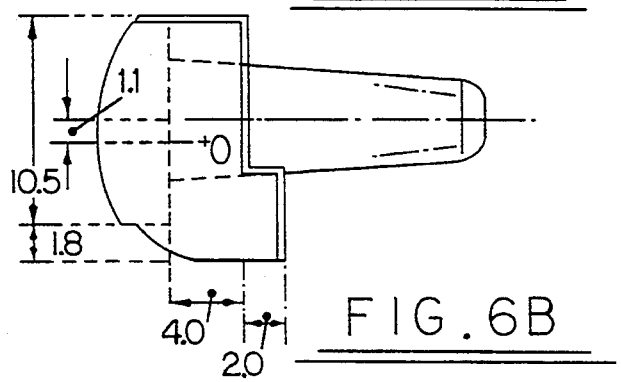
FIG. 6B
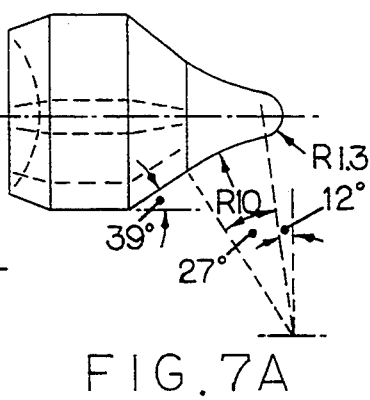
FIG. 7A
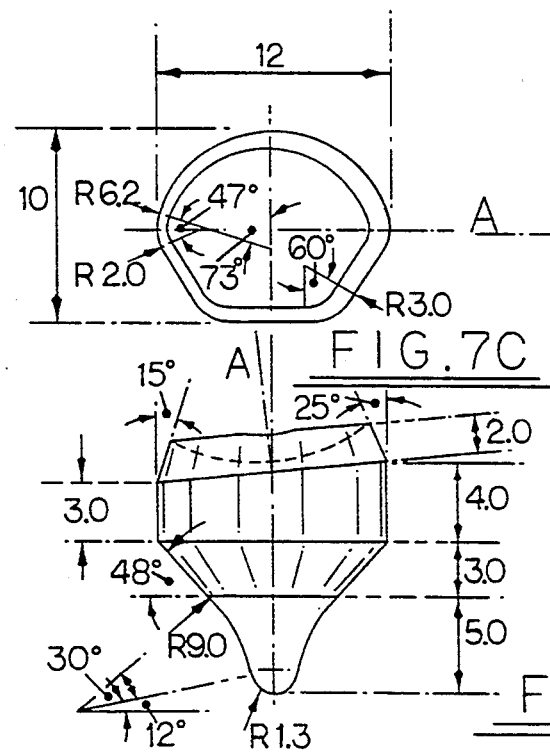
FIG. 7C
FIG. 7B

METACARPAL-PHALANGEAL (MCP) JOINT PROSTHESIS

This invention relates to a joint prosthesis for the human or animal body. More particularly, the invention relates to a prothesis for the metacarpal-phalangeal (MCP) joint of the index finger of the human hand.

There have been many proposals for joint prostheses (including MCP joint prostheses), for example as disclosed in U.S. Pat. Nos. 4,231,121, 4,725,280, 4,731,087, UK 1304837 and EP 310483, but most of these have failed to mimic the natural joint and have resulted in unnatural joint movements and appearance. Natural joints are mechanically complex and provide complex joint movements arising from the control imposed by the natural ligaments, tendons and muscles in the vicinity of the joint.

It is an object of the present invention to provide a new and improved joint prosthesis particularly, but not exclusively, for metacarpal-phalangeal joint replacement.

According to the present invention there is provided a joint prosthesis for a human or animal body, comprising first and second components each made of bio-compatible material and adapted for secural to respective bones of the body in the vicinity of a natural joint after surgical excision of the natural joint, the components of the prothesis being unattached to each other and, in use, being held together to form the joint by the natural ligaments, tendons and muscles of the body in the vicinity of the natural joint.

The first component comprises a stem for reception by a bone cavity and a bulbous head presenting a three-dimensionally curved convex articulation surface which in at least one plane has a radius of curvature which changes within the arc length of the surface and in that plane the length of said arc being at least 90°, and the second component comprises a stem for reception by a bone cavity and a head presenting a three-dimensionally curved concave articulation surface, said concave surface being dimensioned to slide over said convex surface substantially along said 90° arc length to provide flexing movement of the prosthetic joint with the instantaneous centre of rotation of the joint changing during said flexing movement due to said changes of radius of curvature so as to change the distance between the respective bones and thereby allow natural collateral ligament function around the prosthetic joint to aid flexor muscle effect when the joint is extended and extensor muscle effect when the joint is flexed.

Preferably, the concave articulation surface is also capable of sliding movements across the convex articulation surface in directions orchogonal to said plane, said movements being limited in extent by the collateral ligaments of the joint and being substantially less in the joint-flexed condition than in the joint-extended condition due to ligament tension in the flexed condition arising from the aforesaid change of radius of curvature.

Preferably also, said bulbous head of said first component comprises a single lateral protrusion for differentially controlling ligament tension when the joint is in the flexed condition.

Preferably, the convex articulation surface forms part, of an ellipsoid or substantially an ellipsoid whereby said radius of curvature changes occur progressively or substantially progressively along said arc length, and the concave articulation surface forms part of a hollow spheroid or substantially a hollow spheroid, the latter having a curvature which substantially matches that of the former when the joint is midway between its extended and flexed conditions, providing peripheral contact when the joint is in its extended condition and central contact when the joint is in its flexed condition.

The convex articulation surface may have said arc in said one plane formed by two conjoined arc portions having constant but different radii of curvature, the arc portions being arranged with minimal disconformity at their intersection.

An embodiment of the present invention will now be described by way of example with reference to the accompanying drawings, in which FIG. 1 schematically illustrates a human hand in coronal plane view incorporating a joint prosthesis for one finger in accordance with the present invention;

FIG. 2 illustrates a sagittal plane view of part of the FIG. 1 finger with its prosthetic joint in the extended condition;

FIG. 3 shows the joint of FIG. 2 in the flexed condition;

Figure 4A:
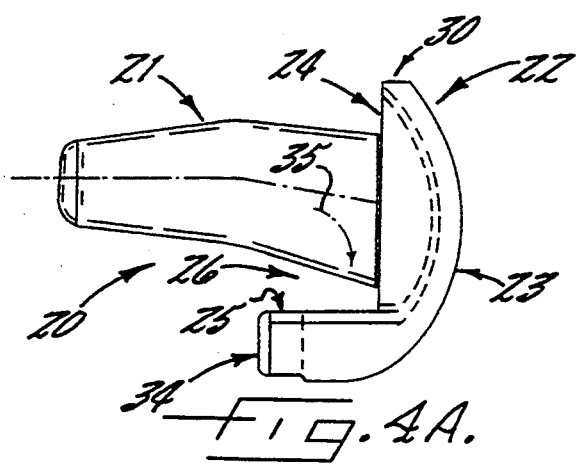
Figure 4C:
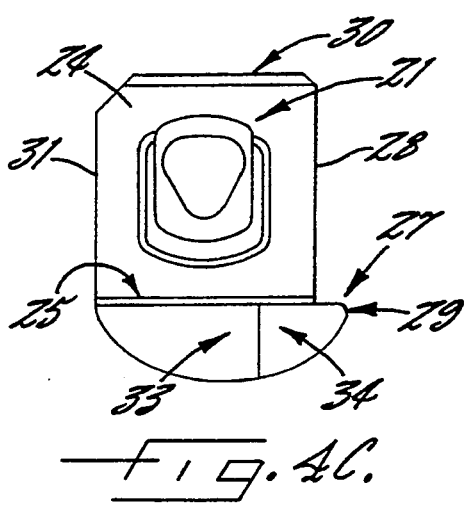
Figure 4B:
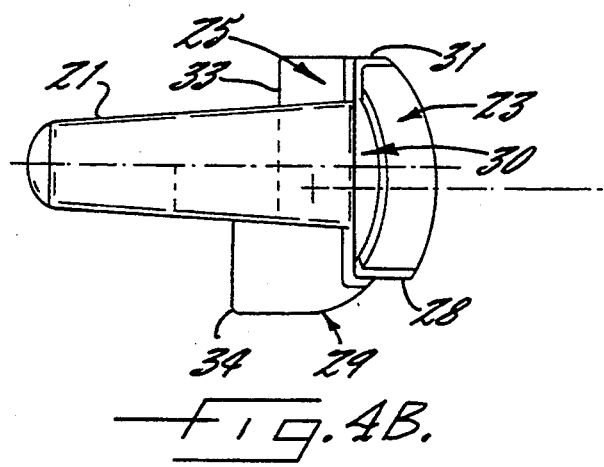
Figure 5C:
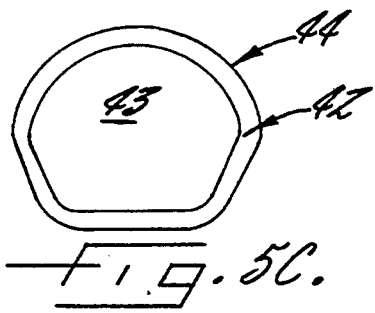
Figure 5A:
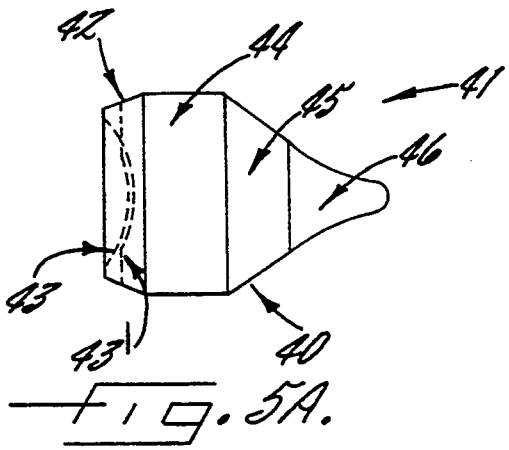
Figure 5B:
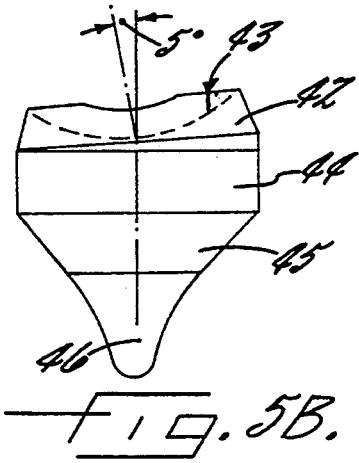
Figure 9C:
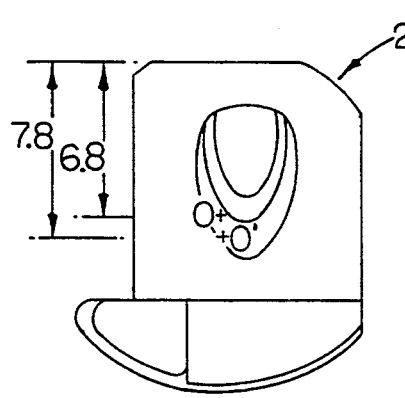
Figure 9A:
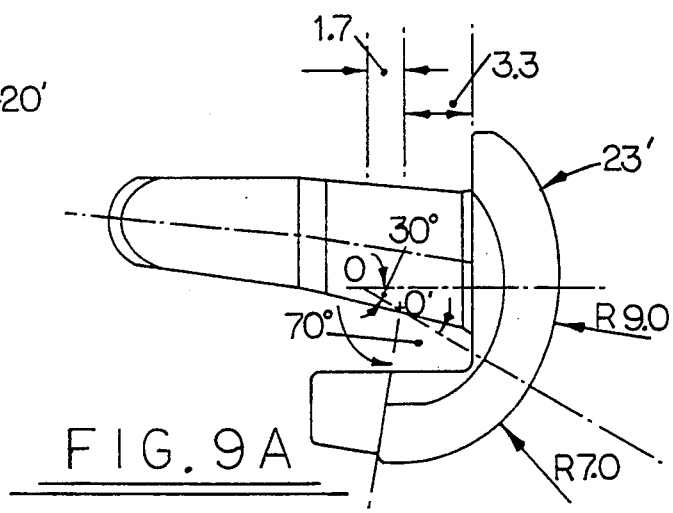
Figure 9B:
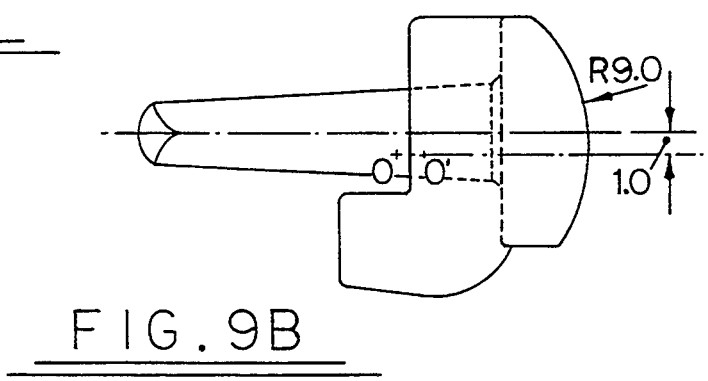

FIGS. 4A, 4B and 4C respectively show sagittal, coronal and transverse views of one component of the prosthetic joint:

FIGS. 5A, 5B and 5C respectively show sagittal, coronal and transverse views of the other component of the prosthetic joint;

FIGS. 6A, 6B and 6C are the same as FIGS. 4A, 4B and 4C but contain dimensional data;

FIGS. 7A, 7B and 7C are the same as FIGS. 5A, 5B and 5C but contain dimensional data;

FIG. 8 illustrates a coronal plane view of part of the FIG. 1 finger with its prosthetic joint in the extended condition; and FIGS. 9A, 9B and 9C respectively show sagittal, coronal and transverse views of a minor modification to the component of FIGS. 4A, 4B and 4C and containing dimensional data.

Turning now to the drawings a human hand 10 is shown in FIG. 1 from the dorsal side (ie from the back of the hand) with the first or index finger 11 containing a joint prosthesis 12 intermediate the metacarpal bone 13 and the phalangeal bone 14. The joint containing the prosthesis 12 accordingly forms part of the "knuckle" at the interface between the palm and the fingers and, as will be explained, permits limited movement of finger 11 in the coronal plane ie towards and away from the adjacent finger 15, together with 90° of flexing movement in the sagittal plane ie towards and away from the palm of the hand. FIGS. 2 and 3 show the extent of the flexing movement.

The prosthesis 12 comprises a first component 20 illustrated in FIGS. 4A, 4B and 4C which is adapted for secural to the metacarpal bone 13 after surgical excision of the natural joint, and a second component 40 illustrated in FIGS. 5A, 5B, 5C adapted for secural to the phalangeal bone 14. Components 20, 40 are unattached to each other and, in use, are held together to form the joint by the natural ligaments, tendons and muscles of the hand in the vicinity of the natural joint.

The natural joint is formed at dotted outline 16 shown in FIGS. 2 and 3 by the bulbous end surface of the bone 13 engaging a concave surface formed at the end of the bone 14 and is held together for articular movement by the extensor muscle tendons 17 on the dorsal side, the flexor muscle tendons 18 on the palmer side, the intrinsic muscles (not shown) on each radial side of the joint, and by a pair of collateral ligaments 19 attached to bones 13, 14 very close to the joint.

Prosthesis component 20 comprises a stem 21 shaped for reception by the bone cavity of the metacarpal bone 13 and a bulbous head 22 which presents a three dimensionally curved convex articulation surface 23 and in the sagittal plane surface 23 has a radius of curvature which changes along the length of the surface arc in that plane as can be seen from FIG. 4A whilst the length of the arc is at least 90°. Stem 21 is integral with head 22 and projects from a substantially planar first rear surface 24 of head 22 which is orthogonal to a planar second rear surface 25 and that portion of the stem 21 which is adjacent surface 25 is inclined at an acute angle (in the region of 10°) thereto to form a wedge-shaped recess 26 for accommodating part of the metacarpal bone 13. The component 20 is fitted to the bone 13 by surgical excision of the bone essentially along two orthogonal planes so that one cut surface abuts first rear surface 24 and the other cut surface of the bone abuts the second rear surface 25 whilst stem 21 penetrates into the bone cavity substantially to engage the walls thereof in an interference fit. It will be understood that the metacarpal bone 13 is essentially of significant strength along its length. Cement, for example, adhesive cement, may also be used to assist location of the implant and it will be understood that the bone cavity requires to be at least partly reamed out to accommodate the stem 21.

Component 20 is additionally provided with a notch 33 cut in that portion of the head 22 containing the surface 25 effectively to provide the lateral protrusion 27 with a rearwardly extending protrusion 34.

Component 40 is fitted to the phalangeal bone 14 without excision of that bone other than removal of its natural concave articulation surface in order to retain the naturally strong perimetrical bone region 14A (FIG. 2) and use that region as the principal support for component 40. Component 20 is located such that its articulation surface 23 is displaced in the proximal direction (ie towards the wrist) from the outline 16 of the natural joint. This is effected in order that component 40 may protrude from the surrounding bone sufficiently to minimise the possibility of bone region 14A making contact with articulation surface 23 throughout use of the joint.

Component 40 comprises a stem 41 for reception by the bone cavity of the phalangeal bone 14 and a head 42 which presents a three dimensionally curved concave articulation surface 43 which is generally spheroidal in nature. Head 42 protrudes from stem 41 which has a generally parallel-sided main portion 44 peripheraly dimensioned and shaped as shown in FIG. 5C, to fit within the perimetrical bone region 14A, a generally conical portion 45 and a rounded end portion 46 both of which extend within the bone cavity and are shaped and dimensioned to be a good fit thereto. With this arrangement head 42 protrudes from the bone 14 and articulation surface 43 is engageable with articulation surface 23 of component 20 without alteration of the length or positioning of the ligaments 19 and muscle tendons 17, 18. Component 40 is made of a more malleable material than component 20 and as a result articulation surface 43 tends to distort through prolonged usage to the shape shown in FIGS. 5A, 5B at 43' and since part of the wear on surface 43 is at its periphery head 42 is slightly coned in order to keep bone portion 14A clear of articulation surface 23 throughout use of the prosthetic joint.

The articulation surface 23 approximates to a part elliptical shape whereas the articulation surface 43 approximates to a part spheroidal shape the latter having a curvature which substantially matches that of the former in the sagittal plane when the joint is approximately midway between its extended condition (FIG. 2) and its flexed condition (FIG. 3), providing peripheral contact on surface 43 in the extended condition and central contact on surface 43 in the flexed condition. It is for this reason that surface 43 wears to the 43' shape. Additionally however due to the fact that the radius of curvature of surface 23 changes progressively along the length of the surface arc in the sagittal plane the instantaneous centre of rotation of the joint changes progressively during flexing movement along locus line 35 (FIG. 4A). The change in radius of curvature changes the distance between the ends of the collateral ligaments 19. These changes are in the nature of increases as the joint moves from the extended condition (FIG. 2) to the flexed condition (FIG. 3) and as a result of increasing tension in the ligaments 19 the natural ligament function occurs which resists lateral movement in the flexed joint. Additionally the changing centre of rotation aids the effect of the flexor muscle tendon 18 when the joint is extended and aids the extensor muscle tendon 17 when the joint is flexed due to the mechanical moment effect.

Articulation surfaces 23, 43 are also curved in the coronal plane and the component 40 is accordingly capable of articulation movement in that plane. This movement however is limited in extent by the two collateral ligaments 19 (one being on either side of the joint) which are capable only of a very small amount of extension (about 6%). The range of articulation in the coronal plane is greatest when the joint is in its extended condition, decreases as the joint is flexed, and is substantially zero when the joint is in its flexed condition. This occurs because of the increasing ligament tension previously referred to arising from the changing centre of rotation of the joint leaving a decreasing availability of ligament tension (or extension) for coronal plane articulation. Likewise component 40 is capable of axial rotation which is limited by the ligaments 19 and the muscle tendons 17, 18 and which is greatest when the joint is in extended condition and least when the joint is in flexed condition.

The bulbous head 22 of the component 20 is also provided with a single lateral protrusion 27 from planar surface 25, as a result of a planar edge face 28 on the head 22 in a plane orthogonal to surfaces 24 and 25. This protrusion 27 enables differential control of ligament tension so that as the joint is flexed the ligament 19 which grazes face 28 is forced by the edge formed between surface 25 and surface 23 to ride out to the outermost coronal edge 29 of the protrusion 27. This constitutes a second factor in lengthening the one ligament which is therefore tensioned to a greater degree than the other ligament when the joint is in its fully flexed condition and is particularly provided on the thumb side of the joint to enhance 'thumb opposition' gripping action. The other collateral ligament grazes planar face 31 which extends parallel to face 28 and these two faces 28, 31 render component 20 relatively compact in its transverse direction as shown in FIG. 4C. Furthermore the uppermost part of the head 22 in the sagittal plane (FIG. 4A) is provided with a planar face 30 to enable the extensor muscle tendon 17 to be relatively flat as it passes over the joint thereby aiding the appearance of the prosthetic joint by avoidance of unnatural bulging.

In the component 40 an aid to natural joint appearance is provided by the centre of curvature of the articulation surface 43 as viewed in the coronal plane (FIG. 5B) being angularly offset by about 5° from the longitudinal axis of the component in order to provide an angular see of the phalangeal bone 14 with respect to the metacarpal bone 13 as shown in FIG. 8 in the direction away from the thumb in a manner which mimics the natural joint. As an alternative to the 5° angular offset the same effect can be achieved with a linear offset of the axis of component 40 with respect to the axis of component 20.

In order to provide the component 20 with a secure fitting to the bone 13 stem 21 is generally tapered along its length and as viewed in the sagittal plane (FIG. 4A) the stem has a bent axis. The stem cross-section varies along the length of the stem from generally square adjacent to head 22 to generally triangular adjacent the stem end as is shown in FIG. 4C in order to maximise contact with the comparatively spongy bone wall near the joint, and the strong cortex elsewhere. This enables maximum penetration of the stem 21 along the cavity of the bone 13 and enables continuous stress to be imposed on the bone 13 particularly where it enters the wedge shaped recess 26 which stimulates bone regeneration. Furthermore, twisting of the component 20 is prevented with respect to the bone 13 by face 25, and the stem 21, due to its sectional shape and bent axis.

Component 40 is securely fitted to the bone 14 with coned surface 45 functioning as a stress control surface and rounded surface 46 functioning as a locator surface. Parallel sided portion 44 of stem 41 abuts the strong bone portion 14A and provides continuous stress thereon which stimulates bone regeneration.

Components 20, 40 are of course made of bio-compatible materials known to have sufficient strength in the art. For example component 20 may be made of cast metal or ceramic and component 40 may be made of high density polyethylene.

Specific dimensional data for components 20, 40 as designed for the index finger of the left hand is provided in FIGS. 6A, 6B, 6C, 7A, 7B, 7C. The dimensions are given in millimetres with a tolerance of ±0.2 mm and angular dimensions are given in degrees with a tolerance of ±2°. The point 'o' in FIGS. 6A, 6B and 6C is the centre of the ellipsoid surface 23 and has an axial radius of 6 mm and coronal and sagittal radii of 8 mm. The point 'A' in FIGS. 7A, 7B and 7C is the centre of the articulation surface 43 which in this instance is ellipsoidal, having a radius of 8 mm in the coronal plane and 6 mm in the other planes.

FIGS. 9A, 9B and 9C provide dimensional data for a minor modification 20' of the component 20 and as designed for the index finger of the right hand. In this design the articulation surface 23' is formed by two conjoined toroidal arc portions, one having a radius of curvature of 9 mm and the other having a radius of curvature of 7 mm. The two arc portions are arranged with minimal disconformity at their intersection and component 20' is used with component 40 (handed for the right hand). In FIGS. 9A, 9B, 9C "O" is the centre of the 9 mm radius and "O'" is the centre of the 7 mm radius.

We claim:

1. A metacarpal-phalangeal MCP joint prosthesis for a human or animal body, comprising first (20) and second (40) components each made of bio-compatible material and adapted for secural to respective bones (13,14) of the body in the vicinity of a natural MCP joint (16) after surgical excision of the natural MCP joint (16), the components (20,40) of the prosthesis (12) being unattached to each other and, in use, being held together to form the prosthetic joint by the natural ligaments, tendons and muscles of the body in the vicinity of the MCP natural joint (16), said first component (20) comprising a stem (21) sized for reception by a metacarpal bone cavity and a bulbous head (22) presenting a substantially-spheroidally curved convex articulation surface (23) which in the sagittal plane has a radius of curvature which changes within the arc length of the surface and in that plane the length of said arc being at least 90°, said bulbous head (22) further comprising a single lateral protrusion (27) extending in the coronal direction and being sized for differentially controlling tension of the collateral ligaments when the prosthetic joint is in the flexed condition, and said second component (40) comprising a stem (41) sized for reception by a phalangeal bone cavity and a head (42) presenting a concave articulation surface (43), said concave surface (43) forming part of a substantially hollow spheroid and being dimensioned to slide over said convex surface (23) substantially along said 90° arc length in the sagittal plane to provide flexing movement of the prosthetic joint with the instantaneous center of rotation of the joint changing during said flexing movement due to said changes of radius of curvature so as to change the distance between the respective bones (13,14) and thereby allow natural collateral ligament function around the prosthetic joint to aid flexor muscle effect when the joint is extended and extensor muscle effect when the joint is flexed, said concave articulation surface (43) having a curvature which provides only ring-like peripheral contact with the substantially-spheroidally curved convex articulation surface (23) when the joint is in its extended condition and only central contact when the joint is in its flexed condition.

2. The metacarpal-phalangeal MCP joint prosthesis as defined in claim 1, wherein the concave articulation surface (43) is configured to permit sliding movements across the convex articulation surface (23) in directions orthogonal to said sagittal plane, said movements being limited in extent by the collateral ligaments of the prosthetic joint (16) and being substantially less in the joint-flexed condition than in the joint-extended condition due to ligament tension in the flexed condition.

3. The metacarpal-phalangeal MCP joint prosthesis as defined in claim 1 wherein the radius of curvature within said arc length of said articulation surface (23) changes progressively along said arc length.

4. The metacarpal-phalangeal MCP joint prosthesis as defined in claim 1 wherein the radius of curvature within said arc length of said articulation surface (23) is formed by two conjoined arc portions having constant but different radii of curvature, with said arc portions being arranged to provide no significant discontinuity at their intersection.

5. A metacarpal-phalangeal MCP joint prosthesis for a human or animal body, comprising first (20) and second (40) components each made of bio-compatible material and adapted for secural to respective bones (13,14) of the body in the vicinity of a natural MCP joint (16) after surgical excision of the natural MCP joint (16), the components (20,40) of the prosthesis (12) being unattached to each other and, in use, being held together to form the prosthetic joint by the natural ligaments, tendons and muscles of the body in the vicinity of the MCP natural joint (16), said first component (20) comprising a stem (21) sized for reception by a metacarpal bone cavity and a bulbous head (22) presenting a substantially-spheroidally curved convex articulation surface (23) which in the sagittal plane has a radius of curvature which changes within the arc length of the surface and in that plane the length of said arc being at least 90°, said bulbous head (22) comprising oppositely facing planar edge faces (28, 31) lying parallel to the sagittal plane and further comprising a single lateral protrusion (27) extending outwardly in the coronal direction from one (28) of said planar edge faces and being sized and positioned for differentially controlling tension of the collateral ligaments when the prosthetic joint is in the flexed condition, and said second component (40) comprising a stem (41) sized for reception by a phalangeal bone cavity and a head (42) presenting a concave articulation surface (43), said concave surface (43) forming part of a substantially hollow spheroid and being dimensioned to slide over said convex surface (23) substantially along said 90° arc length in the sagittal plane to provide flexing movement of the prosthetic joint with the instantaneous center of rotation of the joint changing during said flexing movement due to said changes of radius of curvature so as to change the distance between the respective bones (13,14) and thereby allow natural collateral ligament function around the prosthetic joint to aid flexor muscle effect when the joint is extended and extensor muscle effect when the joint is flexed.

* * * * *